US010552669B2

(12) United States Patent
Lochmann

(10) Patent No.: US 10,552,669 B2
(45) Date of Patent: Feb. 4, 2020

(54) SYSTEM AND METHOD FOR SUPPORTING AN EXERCISE MOVEMENT

(75) Inventor: Matthias Lochmann, Neunkirchen am Brand (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 627 days.

(21) Appl. No.: 14/345,962

(22) PCT Filed: Sep. 20, 2011

(86) PCT No.: PCT/EP2011/066263
§ 371 (c)(1),
(2), (4) Date: Jun. 4, 2014

(87) PCT Pub. No.: WO2013/041123
PCT Pub. Date: Mar. 28, 2013

(65) Prior Publication Data
US 2014/0330410 A1  Nov. 6, 2014

(51) Int. Cl.
*G06K 9/00* (2006.01)
*G09B 19/00* (2006.01)
*A63B 24/00* (2006.01)

(52) U.S. Cl.
CPC ..... *G06K 9/00342* (2013.01); *G09B 19/0038* (2013.01); *A63B 24/0021* (2013.01); *A63B 2225/50* (2013.01)

(58) Field of Classification Search
CPC ........... A63B 2225/50; A63B 24/0021; G09B 19/0038; G06K 9/00342
USPC ....................................................... 434/247
See application file for complete search history.

(56) References Cited

U.S. PATENT DOCUMENTS

| 5,554,033 A | 9/1996 | Bizzi et al. |
| 5,846,139 A * | 12/1998 | Bair .................. A63B 24/0021 434/252 |
| 7,018,211 B1 | 3/2006 | Birkhoelzer et al. |
| 7,302,288 B1 | 11/2007 | Schellenberg |
| 2002/0187846 A1* | 12/2002 | Funk .................. A63B 24/0003 473/219 |
| 2004/0147329 A1 | 7/2004 | Meadows et al. |

(Continued)

FOREIGN PATENT DOCUMENTS

| CN | 101014240 | 8/2007 |
| CN | 101014240 A | 8/2007 |

(Continued)

OTHER PUBLICATIONS

Kneissler M. et al., "Concept and Clinical Evaluation of Navigated Control in Spine Surgery," Advanced Intelligent Mechatronics, 2003. Proceedings. 2003 IEEE/ASME International Conference on Jul. 20-Jul. 24, 2003, Piscataway, NJ, USA, IEEE, vol. 2, Jul. 20, 2003 (Jul. 20, 2003), pp. 1084-1089.

*Primary Examiner* — Jack Yip
(74) *Attorney, Agent, or Firm* — Mannava & Kang, P.C.

(57) ABSTRACT

The invention relates to a system for supporting an exercise movement, comprising an object, a detection device (101) for detecting an actual position of the object, a determination device (103) for determining a desired position of the object, and a display device (105) for displaying information on the desired position if the actual position and the desired position are different from each other.

30 Claims, 13 Drawing Sheets

(56) References Cited

U.S. PATENT DOCUMENTS

| | | | |
|---|---|---|---|
| 2004/0236506 A1 | 11/2004 | Kolb et al. | |
| 2005/0012023 A1* | 1/2005 | Vock | A63B 24/0003 250/206.1 |
| 2005/0101415 A1 | 5/2005 | Sweeney | |
| 2006/0047428 A1* | 3/2006 | Adams | G01C 21/16 701/300 |
| 2008/0262660 A1* | 10/2008 | Weber | G06F 17/3087 701/1 |
| 2008/0312010 A1* | 12/2008 | Marty | A63B 24/0003 473/447 |
| 2009/0060352 A1* | 3/2009 | Distante | A63B 24/0021 382/224 |
| 2009/0091583 A1* | 4/2009 | McCoy | A63F 13/02 345/633 |
| 2009/0102746 A1 | 4/2009 | Fisher et al. | |
| 2009/0275371 A1* | 11/2009 | Takahashi | A63F 13/10 463/3 |
| 2009/0298588 A1* | 12/2009 | Gopinath | A63B 24/0021 463/36 |
| 2010/0026809 A1* | 2/2010 | Curry | H04N 5/222 348/157 |
| 2010/0201500 A1* | 8/2010 | Stirling | A61B 5/1127 340/407.1 |
| 2012/0088633 A1* | 4/2012 | Crafton | A63B 22/0235 482/1 |
| 2012/0283080 A1 | 11/2012 | Mayr | |

FOREIGN PATENT DOCUMENTS

| | | |
|---|---|---|
| JP | H10502465 | 3/1998 |
| JP | 2002-186702 A | 7/2002 |
| JP | 2003-164544 A | 6/2003 |
| JP | 2006190237 A | 7/2006 |
| JP | 2006204730 A | 8/2006 |
| JP | 2009-219633 A | 10/2009 |
| JP | 2010517731 | 5/2010 |
| NZ | 249799 A | 11/1996 |
| WO | 2011051470 | 5/2011 |

* cited by examiner

SYSTEM AND METHOD FOR SUPPORTING AN EXERCISE MOVEMENT

PRIORITY

The present application claims priority under 35 U.S.C. § 371 to PCT Application PCT/EP2011/066263, filed on Sep. 20, 2011, the disclosures of which are hereby incorporated by reference in their entireties.

BACKGROUND OF THE INVENTION

The present invention relates to the field of movement exercises within the scope of sport and rehabilitation.

Human movement is a complicated biomechanical sequence. Thus, for example, an athlete using a sports object, such as a ball or a piece of throwing equipment, needs to practice these motion sequences, which lead to an ideal sports result, during training. The situation is substantially more complicated in the case of so-called team sports, wherein e.g. a technical-tactical interaction of athletes amongst themselves and with a piece of playing or throwing equipment needs to be practiced during training.

Technical devices, which e.g. enable a video analysis of a game that has already taken place, are known for training analysis purposes. Such a video analysis assists in being able to make a statement relating to the movements of the individual players with respect to one another and with respect to the ball.

A disadvantage of such devices consists of the fact that they cannot be used for supporting the movement exercise in real time. For this reason, such devices are also unsuitable in the field of rehabilitation, where it is particularly important to support a rehabilitation patient already during the support of a movement exercise.

It is therefore the object of the present invention to develop a concept for supporting a movement exercise in real time.

This object is achieved by the features of the independent claims. Advantageous development forms are the subject matter of the dependent claims, the description and the figures.

BRIEF SUMMARY OF THE INVENTION

The present invention is based on the discovery that the object above can be realized by determining and indicating an intended position of the object, provided that the intended position differs from the actual position of the object. By way of example, this renders it possible already during training to indicate in real time a connecting line between the center of the goal and the ball to a goalkeeper, who constitutes the object in accordance with one embodiment, as a goalkeeper intended position. This allows the goalkeeper to coordinate his movement with respect to the geometry of the pitch more quickly. If the object is the ball, it is possible to indicate in real time an intended position of the ball to e.g. an association football player, depending on a game situation, as a function of the geometric position of a further player.

This allows the quality of the technical-tactical training to be optimized in real time. In particular, a defined target behavior can be made possible on the basis of standard values based on empirical-statistical models and/or based on deterministic models and/or mixed model approaches via permanent real-time feedback within substantially shorter learning and training intervals than would have been possible using existing methods. In particular, the invention can contribute to analyze, both in detail and in real time, complex sequences, e.g. the technical-tactical interaction of athletes amongst themselves or with a piece of playing or throwing equipment, during sports training and control training or a game in real time on the basis of comparing actual and intended value.

By way of example, if a movement exercise is to be carried out with a knee joint as an object during rehabilitation, it is possible for the area of the knee of a rehabilitation patient to be provided with a position sensor which indicates the actual position of the knee. By way of example, if the knee is at an undesired position at a defined time during an exercise, information can be indicated to the rehabilitation patient to the effect that the intended position has not yet been reached or in relation to the direction in which the knee is to be moved in order to reach the intended position. This allows quick rehabilitation advances to be achieved.

The object can be a game object, such as e.g. a football or a tennis racket, the player himself or a body part of the player, such as e.g. his head or his foot. In accordance with some embodiments, the object can be a rehabilitation patient or a body part of the rehabilitation patient, such as e.g. a knee joint or an elbow joint. However, the object can also be a rehabilitation object, such as e.g. a gymnastic ball.

In accordance with a first aspect, the invention relates to a system for supporting a movement exercise with an object, comprising a detection apparatus for detecting an actual position of the object, a determination apparatus for determining an intended position of the object and an indication apparatus for indicating information relating to the intended position if the actual position differs from the intended position.

The information relating to the intended position can comprise an indication of the intended position itself or an indication that the intended position has not yet been reached or an indication of a direction of the intended position. In order to determine whether the actual position differs from the intended position, the determination apparatus can compare the actual position with the intended position. Here, the actual position and the intended position can be available in the form of digital position data.

In accordance with one embodiment, the object is embodied to emit a position signal, in particular a global positioning signal. The detection apparatus is embodied to receive the position signal and determine the actual position of the object on the basis of the received position signal. In order to receive the position signal, the detection apparatus can comprise a reception antenna which receives the position signal. The detection apparatus can furthermore be embodied to process the received position signal in order to detect the actual position of the object.

In accordance with one embodiment, the detection apparatus is embodied to receive a reflection signal, in particular a radar signal or a laser signal, reflected at the object and determine the actual position of the object on the basis of the reflected reflection signal. By way of example, to this end, the object can have a reflecting surface, which may be metallic, to reflect a radar signal.

In accordance with one embodiment, the detection apparatus is embodied to emit a transmission signal, in particular a radar signal or a laser signal, in order to produce the reflection signal. To this end, the detection apparatus can comprise a transmitter, in particular a transmission antenna, which emits a directed or a non-directed transmission signal which is reflected at the object, as a result of which the reflection signal is produced.

In accordance with one embodiment, the determination apparatus is embodied to determine a predetermined position of the object, in particular a predefinable position of the object, as the intended position. By way of example, the predetermined position of the object can be selected from a plurality of possible intended positions. This selection can be random or deterministic. By way of example, the predetermined, deterministic position can be predefined on the basis of a rule.

In accordance with one embodiment, the object is a ball and the determination apparatus is embodied to determine, in particular select, a sensor area of a sensor wall as the intended position.

In accordance with one embodiment, the sensor wall is an element of the system. In accordance with another embodiment, the sensor wall is not an element of the system. The sensor wall can have at least one sensor, e.g. a pressure sensor, for detecting the ball. However, in accordance with one embodiment, the sensor wall can be formed in such a way that the incidence of the ball can be detected e.g. optically by e.g. inward or outward arching of the sensor wall.

By way of example, this renders it possible to indicate an area on the sensor wall which represents a goal to an association football player as intended position of the ball. This allows the association football player to quickly carry out different ball shooting exercises.

In accordance with one embodiment, the system can comprise one or more ball providers, which provide a ball as the object to be conveyed to the sensor area. The ball provider can be embodied to provide the ball in a predetermined direction, e.g. toward the player. The indication apparatus can be formed by the sensor wall, which indicates the sensor area as the intended position.

In accordance with one embodiment, the determination apparatus is embodied to determine the intended position as a function of the actual position of the object. This enables dynamic determination of the intended position as a function of e.g. a game situation on a pitch.

In accordance with one embodiment, the determination apparatus is embodied to determine the intended position as a function of the actual position of the object and a geometric characteristic of an area, in particular of a pitch, within which the object can be moved, or determine the intended position as a function of the actual position of the object in relation to a geometric characteristic of the pitch, in particular of a center of a goal. By way of example, this renders it possible to determine the intended position as a connection line between the center of a goal and the ball as a function of a ball position.

In accordance with one embodiment, the determination apparatus is embodied to determine the intended position on the basis of a rule, in particular on the basis of a biomechanical rule. By way of example, if the object is a body part to be moved of a rehabilitation patient, it is possible to consider the biomechanical characteristic of the human body when determining the intended position. However, the biomechanical rule can also comprise the age of the rehabilitation patient or his basic mobility. This can render it possible to avoid unachievable intended positions from being determined and indicated.

In accordance with one embodiment, the determination apparatus is embodied to determine the intended position as a sequence of successive auxiliary positions. As a result of the successive sequence of the auxiliary positions, step-by-step reaching of a final intended position is simplified because e.g. relatively small movement steps can be practiced.

In accordance with one embodiment, the detection apparatus is embodied to determine a further actual position of a further object and the determination apparatus is embodied to determine the intended position of the object as a function of the further actual position, in particular relative to the further actual position of the further object. If the object is a player, the further object can be another player, as a result of which it is possible to practice the movement of the player with respect to the further player. By way of example, if the object is a ball, the further object can be a player, e.g. a goalkeeper, and vice versa. This allows the intended position of the ball or of the player to be determined e.g. dynamically and indicated as a function of the further intended position.

In accordance with one embodiment, the determination apparatus is embodied to determine the intended position on the basis of a predetermined rule which links the intended position to an actual position. By way of example, the rule can link the intended position of one player with respect to the further actual position of a further player.

In accordance with one embodiment, the object and the further object are skis. By way of example, this renders it possible to indicate a position of the skis with respect to one another, in particular in the case of ski jumping.

In accordance with one embodiment, the detection apparatus is embodied to determine a plurality of further actual positions of a plurality of further objects and the determination apparatus is embodied to determine the intended position of the object as a function of the plurality of the further actual positions. The plurality of further actual positions can e.g. be determined by actual positions of players of a team. This allows the intended position of an individual player to be determined and/or indicated with respect to the team.

In accordance with one embodiment, the determination apparatus is embodied to determine a centroid, in particular a geometric or weighted centroid, of the further actual positions and determine the intended position as a function of the centroid, in particular relative to the centroid. By way of example, the geometric centroid can be determined on the basis of any algorithm known per se, which enables a geometric centroid to be determined. By way of example, the weighted centroid can be a geometric centroid of actual positions of the further objects, which are weighted in accordance with one embodiment. By way of example, the weighting can express the importance of a player, e.g. of a goalkeeper, for a specific game situation.

In accordance with one embodiment, the determination apparatus is embodied to determine the intended position as a function of the geometric centroid on the basis of a predetermined rule which links intended positions to geometric centroids. By way of example, this rule can be created on the basis of empirical values.

In accordance with one embodiment, the indication apparatus is embodied to indicate the intended position itself as information relating to the intended position or information relating to the positioning of the intended position with respect to positioning of the object, in particular with respect to a direction in relation to the intended position, or as information relating to a difference between the actual position and the intended position. By way of example, the difference can be indicated by an acoustic signal, for example a beat or a signal in which the frequency changes, wherein the beat frequency or the signal frequency depend directly on the difference.

In accordance with one embodiment, the indication apparatus is embodied to indicate the information relating to the intended position by acoustic, optical, acousto-optical, tactile means, in particular by means of a vibration or a pressure. To this end, the indication apparatus can be portable by e.g. a user in order to generate e.g. a tactile signal which indicates the information relating to the intended position to the user, e.g. player. However, the indication apparatus can comprise a screen or be embodied to project the information onto the projection onto a projection area, e.g. onto a pitch or onto a visor screen of a helmet visor.

In accordance with one embodiment, the object is a match ball, in particular a football or a table tennis ball or a tennis ball or a rugby ball, or a puck, the indication apparatus comprises a sensor wall for detecting an object impinging on the sensor wall and the indication apparatus is embodied to indicate an area of the sensor wall as information relating to the intended position by means of visual accentuation, in particular by means of a luminous or illuminated area, or by acoustic accentuation. By way of example, the sensor wall can have features of the aforementioned sensor wall or correspond to the aforementioned sensor wall.

In accordance with one embodiment, the indication apparatus comprises a visor or a projection apparatus, in particular a head-up projection apparatus, and the indication apparatus is embodied to indicate the information relating to the intended position on the visor or by projection onto a projection area, in particular onto a visor screen or windscreen, by means of the projection apparatus. By way of example, the indication apparatus can use the head-up projection apparatus to project the information relating to the intended position onto a windscreen of a vehicle or onto a visor screen of a helmet visor.

In accordance with one embodiment, the visor is a visor of a skiing helmet and the indication apparatus is embodied to indicate the information relating to the intended position with respect to the actual position or with respect to at least one of the skis in respect of the other ski on the visor, in particular as intended ski position. This renders is possible to indicate the intended position of the skis with respect to one another directly to a ski jumper during a ski jump. To this end, the skis can be provided with e.g. a transmitter which emits position signals. In this case, the determination apparatus can be arranged in the skiing helmet and receive these signals.

This renders it possible to indicate not only the alignment or position of the skis with respect to one another, but also the actual position of the skis compared to an intended position which, for example, is predefined or determined by a biomechanical model. When determining the intended position, it is possible to consider e.g. the current thermal winds, the side winds, the air density or the flight speed, in particular on the basis of a predefined rule which links the aforementioned variables to intended positions.

In accordance with one embodiment, the object is a vehicle, in particular a sled or a bobsleigh, or a motor vehicle, and the indication apparatus is embodied to indicate the information relating to the intended position as an ideal vehicle line on a visor of a helmet or as projection on a windscreen. The ideal vehicle line according to one embodiment is the driving line which would enable the shortest lap time for the current driving situation.

In accordance with one embodiment, the object is at least one foot of a user, in particular of a golfer, and the indication apparatus is embodied to indicate, in particular project, the information relating to the intended position of at least one of the feet onto an area of ground, on which the user can be positioned. By way of example, the information can be indicated by projection onto the area of ground. In accordance with one embodiment, the area of ground can be provided with e.g. luminous elements, in particular with light-emitting diodes, which e.g. indicate the desired foot position as intended position.

In accordance with one embodiment, the indication apparatus is embodied to indicate the information relating to the intended position on an electronic display. The determination apparatus can be embodied to actuate the display in a suitable manner.

In accordance with one embodiment, the indication apparatus is embodied to actuate the display of a smartphone for indicating the information relating to the intended position.

In accordance with one embodiment, the detection apparatus and/or the determination apparatus and/or the indication apparatus can be realized on such a smartphone, for example in software by means of an application program.

In accordance with one embodiment, the indication apparatus is embodied to project the information relating to the intended position onto a pitch by means of a light, in particular by means of a laser projection or an LED projection.

In accordance with one embodiment, the determination apparatus is embodied to determine the intended position as a function of a body parameter, in particular heart rate, heart rate variability, respiratory frequency, body temperature, blood value parameters such as sugar concentration or oxygen concentration. By way of example, the body parameters can be established by means of contactless sensors and, for example, be transmitted to the detection apparatus.

In accordance with one embodiment, the object is a piece of playing equipment, in particular a racket such as a tennis racket, golf club, table tennis racket, a piece of fencing equipment, a weight, ball, puck, curl, boat, in particular canoe, paddle, a piece of throwing equipment, in particular discus or hammer, bicycle, bicycle element such as handlebar, bow, arrow, shooting equipment, helmet, ice skate, piece of clothing, ski, ski binding, snowboard, vehicle such as sled or bobsleigh or motor vehicle, or shoe.

In accordance with one embodiment, the object is a user, in particular a player, or body part of the user, in particular head, forehead, back of the head, nasion, inion, a preauricular point, cervical spine, thoracic spine, lumbar spine, sternum, shoulder height, joint such as elbow joint or wrist or knee joint or ankle, anterior superior iliac spine, greater trochanter, tip of the foot, heel or navel.

In accordance with one embodiment, the object is the head of a user, wherein the detection apparatus is embodied to detect a plurality of position signals indicating a head position, wherein the determination apparatus is embodied to determine a transversal plane of the head as the actual position of the head and wherein the indication apparatus is embodied to indicate information relating to the intended position situated in the transversal plane, in particular by acoustic or optical or tactile means.

In accordance with one embodiment, the determination apparatus comprises a plurality of position sensors, which can be arranged on the head of a user, for determining the position and outputting position signals, and a plurality of discrete luminous elements, in particular LEDs, for indicating the information relating to a rotational direction of the head in the transversal plane.

In accordance with one embodiment, the determination apparatus comprises at least one position determination apparatus, in particular a position transmitter, for detecting the actual position. By way of example, such a position transmitter can be housed on or in one of the aforementioned skis. In general, this embodiment renders it possible for the system according to the invention to be carried by a user.

In accordance with one embodiment, the system furthermore comprises an object provider, in particular a ball provider or a puck provider, for providing the object.

In accordance with one embodiment, the system comprises a plurality of detection apparatuses for detecting the actual position.

In accordance with a further aspect, the invention relates to a method for supporting a movement exercise with an object, comprising detecting an actual position of the object, determining an intended position of the object and indicating information relating to the intended position if the actual position differs from the intended position.

Further features of the method emerge directly from the functionality of the system or of a feature of the system.

In accordance with one embodiment, the method can be carried out by the system.

In accordance with a further aspect, the invention relates to a computer program with a program code for executing the method according to the invention when the program code is executed on a computer.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE SEVERAL VIEWS OF THE DRAWING(S)

Further exemplary embodiments of the invention will be explained in more detail with reference being made to the attached drawings. In detail:

It is to be understood that both the foregoing general description and the following detailed description are exemplary and explanatory only, and are intended to provide an explanation of various embodiments of the present teachings.

DETAILED DESCRIPTION OF THE INVENTION

Figure 1:
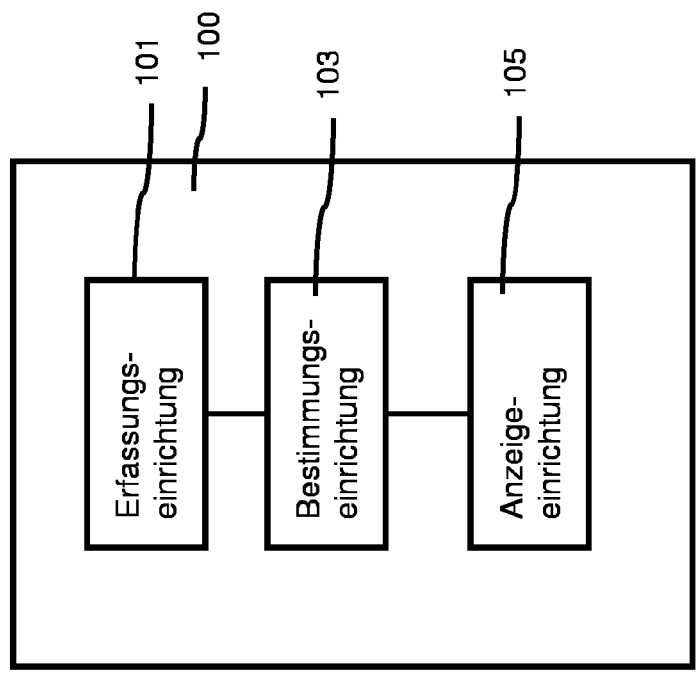
FIG. 1 shows a block diagram of a system for supporting a movement exercise with an object in accordance with one embodiment.

FIG. 1 shows a block diagram of a system 100 for supporting a movement exercise with an object. The system 100 comprises a detection apparatus 101 for detecting an actual position of the object, a determination apparatus 103 for determining an intended position of the object and an indication apparatus 105 for indicating information relating to the intended position if, for example only if, the actual position differs from the intended position.

The following table 1 shows a few exemplary embodiments of objects for various sports.

TABLE 1

| Sport or discipline | Object |
| --- | --- |
| Badminton | Badminton racket |
| Basketball | Basketball |
| Archery | Bow, arrow |
| Boxing | Boxing gloves, boxing shorts, punching bag, speed ball |
| Fencing | Saber, helmet, sports attire |
| American football | Football |
| Association football | Ball |
| Weightlifting | Bar, weights |
| Golf | Clubs, shoes, sports attire |
| Handball | Ball |
| Hockey | Hockey stick, ball |
| Judo | Belt, sports attire |
| Canoe sport - canoe racing | Canoe, poles in the water, gates |
| Canoe sport - canoe slalom | Canoe, poles in the water, gates |
| Track and field | Discus, javelin, hammer |
| Modern pentathlon | Pistol, epée, swimming trunks, swimming cap, horse, saddle, riding hat, horseshoe, obstacle, running shoe |
| Cycling - track cycling | Bicycle, frame, handlebar, wheels, saddle |
| Cycling - BMX | Bicycle, frame, handlebar, wheels, saddle |
| Cycling - mountain bike (cross country) | Bicycle, frame, handlebar, wheels, saddle |
| Cycling - road race | Bicycle, frame, handlebar, wheels, saddle |
| Riding - dressage | Saddle, obstacles, riding hat, belt, horseshoe |
| Riding - eventing | Saddle, obstacles, riding hat, belt, horseshoe |
| Riding - jumping | Saddle, obstacles, riding hat, belt, horseshoe |
| Wrestling - freestyle | Sports attire, belt |
| Wrestling - Greco-Roman | Sports attire, belt |
| Rowing | Oar, boat |
| Rugby (7s) | Ball, scrum cap, sports attire |
| Shooting | Bow, arrow |
| Water sports - diving | Swimming trunks |
| Water sports - swimming | Swimming trunks |
| Water sports - synchronized swimming | Swimming trunks |
| Water sports - water polo | Ball, goal |
| Sailing | Mast, boat, rudder |
| Tae kwon do | Sports attire |
| Tennis | Tennis racket |
| Table tennis | Ball, table tennis racket |
| Triathlon | Bicycle, shoes, swimming trunks |
| Gymnastics - artistic gymnastics | Sports attire |
| Gymnastics - rhythmic gymnastics | Ball, club |
| Gymnastics - trampolining | Fabric |
| Volleyball - beach volleyball | Volleyball |
| Volleyball - volleyball | Volleyball |
| Biathlon | Rifle, ski, ski boots, ski attire |

TABLE 1-continued

| Sport or discipline | Object |
| --- | --- |
| Bobsleigh sport - bobsleigh | Bobsleigh, helmet |
| Bobsleigh sport - skeleton | Bobsleigh, helmet |
| Curling | Curl |
| Ice hockey | Puck, sports attire, helmet, goal |
| Ice-skating - figure skating | Ice skate, sports attire |
| Ice-skating - short track | Ice skate, sports attire |
| Ice-skating - speed skating | Ice skate, sports attire |
| Luge | Sled, helmet |
| Skiing - Alpine skiing | Ski, binding, boot |
| Skiing - freestyle skiing | Ski, binding, boot |
| Skiing - Nordic skiing - Nordic combined | Ski, binding, boot |
| Skiing - Nordic skiing - cross-country skiing | Ski, binding, boot |
| Skiing - Nordic skiing - ski jumping | Ski, binding, boot |
| Skiing - snowboard | Snowboard |

The following table 2 shows a few exemplary embodiments of person-related objects.

TABLE 2

| |
| --- |
| Head, forehead, back of head |
| Nasion, inion, preauricular point |
| Cervical spine, thoracic spine, lumbar spine |
| Sternum |
| Shoulder height (acromion) |
| Elbow joint |
| Wrist |
| Anterior superior iliac spine |
| Greater trochanter (trochanter major) |
| Knee joint |
| Ankle |
| Tip of the foot |
| Heel |
| Navel |

Figure 2:
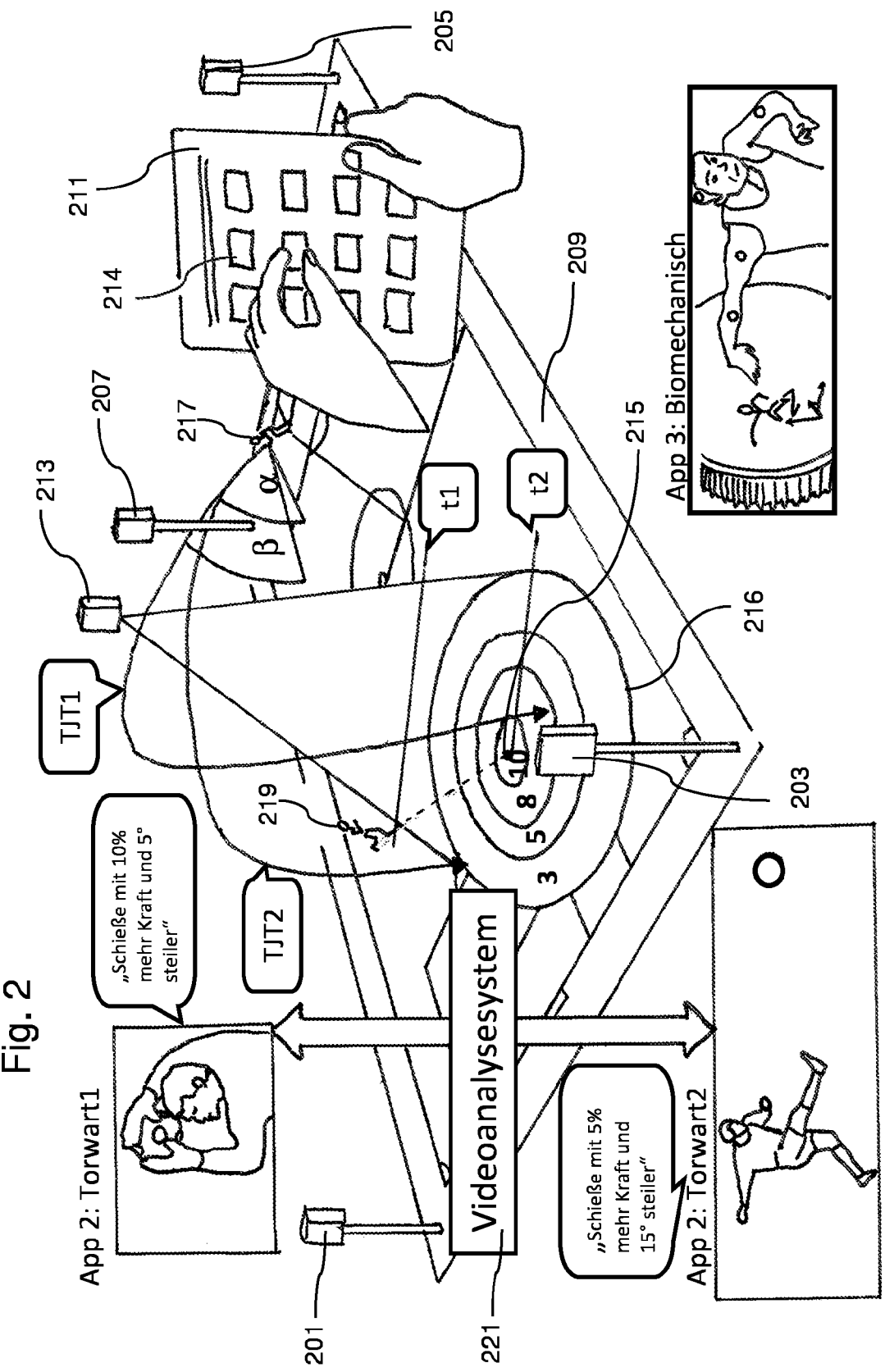
FIG. 2 shows a system for supporting a movement exercise in accordance with one embodiment.

FIG. 2 shows a system for supporting a movement exercise with an object which is e.g. a football. The system comprises a position localization system with a plurality of detection apparatuses 201, 203, 205 and 207 (PLS1, PLS2, PLS3, PLS4), which are arranged at a distance from one another, for example in corners of a football pitch 2109. However, the system can comprise only one, two or three or more than 4 detection apparatuses.

The system furthermore comprises a determination apparatus 211 for determining an actual position of the object corresponding to the current actual position of the object. By way of example, the determination apparatus can be realized on a smartphone by means of an application program having a plurality of application fields 214, which respectively enable a selection of an intended position. However, the determination apparatus 211 can also be a separate computer or a computer cluster.

The system furthermore comprises an indication apparatus 213 for indicating information relating to the intended position, provided the actual position differs from the intended position. By way of example, the intended position 215 can lie in an area 216 of the pitch 209. By way of example, the indication apparatus 213 can be embodied to project concentric circles around the intended position 215 on the pitch in order, for example, to indicate the intended position to a goalkeeper 217. By way of example, the actual position of the object can correspond to the actual position of the goalkeeper 217. By way of example, if a further player 219 is situated on the pitch 209, the intended position 215 can be determined and/or indicated as a function of an actual position of the further player 219. To this end, the further player 219 can be equipped with a transmitter, which transmits a position of the further player 219 to the detection apparatuses 201 to 205 which form a common detection apparatus.

The system can furthermore comprise a video analysis system 221, which, as an application, can indicate the behavior of a first goalkeeper and of a second goalkeeper.

In order to be able to accurately play a ball into the run of an attacker by means of a long throw out, different partial skills of a goalkeeper (TW1) are advantageous. Firstly, this relates to the ability of the goalkeeper to anticipate the expected position of a teammate when the teammate P1 in position 10 receives the ball. Furthermore, with respect to his technical, strength and coordination level, the goalkeeper should be able to drive the ball adequately by means of the following biomechanical influencing variables:
linear momentum
rotational momentum (left, right)
throw-out angle (horizontal, vertical)

The biomechanical influencing variables mentioned here, like the goalkeeper movement, can likewise be detected in real time in a manner known per se.

If the player P1, to whom the ball is to be passed, starts to run in a specific direction with the mean speed v at the time t1, the system is able, on the basis of model assumptions which comprise deterministic biomechanical laws and which can be stored in the database, to calculate, in advance, where the ball would land at the time t2 if said ball is thrown out e.g. with biomechanical initial conditions known in advance so as to land near the foot of the player at the time t2. This target to be actuated in the form of a target disk can be projected onto the pitch or training area by the display apparatus 213 in a permanent or dynamically variable manner. Therefore, the target zone can be visualized for the goalkeeper by means of real-time feedback even before he finally throws out the ball. Likewise, the parameters including throw-out angle alpha and beta, momentum of the ball p, ball trajectory, etc., under the influence of which the ball trajectory came about, are available after short time delay (0.1 s-0.5 s). The target precision of the throw out, for example within the target disk, can also be specified in real time by means of the system. In the learning or real-time feedback mode, the goalkeeper now is able to decide on what basis the feedback should take place. To this end, the goalkeeper or coach makes a selection from various applications (apps) on a tablet PC, PC, notebook, smartphone or other indication instrument. A decision can be made as to whether the intended/actual value of the deviation is brought about on the basis of the statistical data material, which contains the database about the goalkeeper, about whom the database contains data. Alternatively, he can also, referring to different biomechanical models, resort to a real-time training and learning unit. He can then select whether carrying out the throw out should be performed optimized for distance, optimized for precision or optimized for time.

Figure 3:
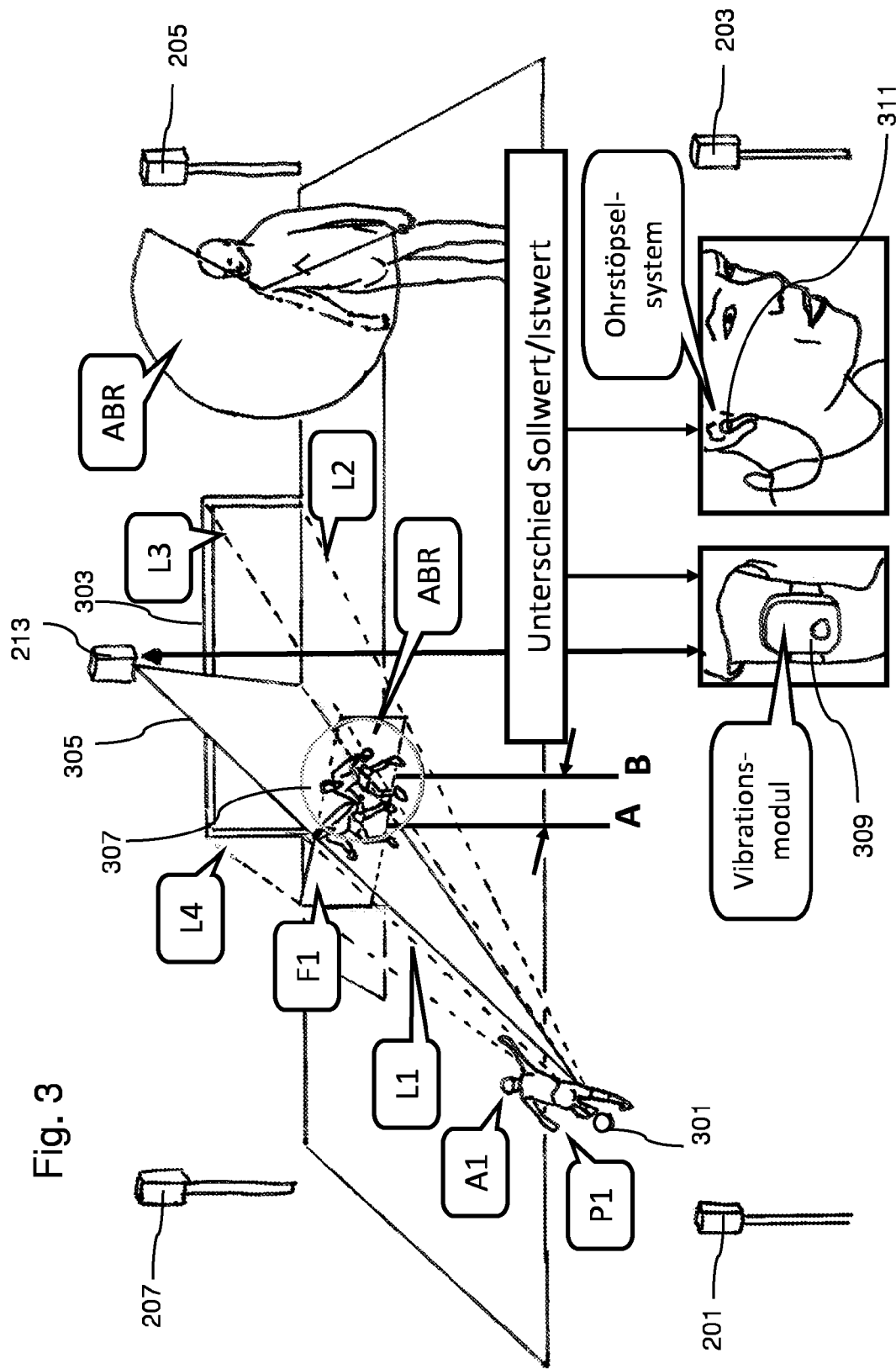
FIG. 3 shows a system for supporting a movement exercise in accordance with a further embodiment.

FIG. 3 shows a system for supporting a movement exercise with an object, for example with a football, in accordance with one embodiment. The system comprises at least one of the detection apparatuses 201 to 207 depicted in FIG. 2. By way of example, these detect an actual position of an object 301, which may be a ball. The determination apparatus, which is not depicted in FIG. 3, for example establishes a connection line 305 between the center of a goal and the actual position of the ball 301 on the basis of the actual position of the ball 301 and the center of the goal 303.

The indication apparatus 213 can be embodied to project the connection line 305 onto the pitch and indicate said line as intended position to a goalkeeper 307, who can be an object within the meaning of the present description in accordance with one embodiment.

In accordance with one embodiment, the indication apparatus 213 can, alternatively or additionally, comprise at least one vibration module 309 indicating the direction toward the connection line 305 to the goalkeeper. To this end, the goalkeeper can carry vibration modules on both sides, for example on the upper arms, and these can indicate vibration information relating to the direction of the connection line 305 as a function of the actual position of a goalkeeper 307.

In accordance with one embodiment, the indication apparatus 213 can, alternatively or additionally, comprise at least one loudspeaker 311 which, for example in the form of an earplug, can be attached for example to the ear of the goalkeeper. The loudspeaker 311 is embodied to emit acoustic signals which provide information about the positioning of the intended position, i.e. which provide information about the positioning of the connection line 305. In accordance with one embodiment, this renders it possible to dispense with the projection of the connection line onto the pitch. In accordance with a different embodiment, it is possible for at least two of the aforementioned embodiments, for example projection and vibration or projection and acoustic signal, to be used together.

By way of example, if the attacker A1 shoots at the goal from the position P1, the ball, in the case of an approximately straight-line ball trajectory, for geometric reasons only enters the goal if it has moved within a space spanned between the ball and the imaginary connection lines (L1-L4). The individual tactical object of the goalkeeper now consists of covering the largest possible sub-area of the area (F1) by his posture and position with his anthropometrically determined range (ABR). He is most successful if he operates on the imaginary line between the center of the ball and the center of the goal. During shooting practice or the game, this line can be projected onto the pitch or training field by means of the indication apparatus 213, which can form an optical-acoustic-tactile feedback system. Since the spatial position of the ball 301 can be transmitted to the system in real time, this line permanently moves with the ball position. Hence, via visual real-time feedback, the goalkeeper can permanently optimize his individual-tactical positional play. Parallel to the visual real-time feedback, there is acoustic feedback by means of a mini earplug system and/or a small loudspeaker system, which is attached to the body of the goalkeeper, and/or by means of a PA system. This audio feedback operates on the basis that, for example, the standard pitch a is played if the correct position is assumed and, in the case of an increasing intended/actual value difference (SID), the frequency is modified proportionally to the distance from the ideal position. In terms of acoustic feedback, the system could likewise work like an echo sounder or like acoustic feedback from a parking assistance system, etc. The third component of the real-time feedback is performed in the form of an intended/actual value difference-controlled modification of the vibration frequency and/or amplitude of a tactile-acoustic feedback system, which is worn on the body of the goalkeeper and may be an element of the indication apparatus 213.

Figure 4:
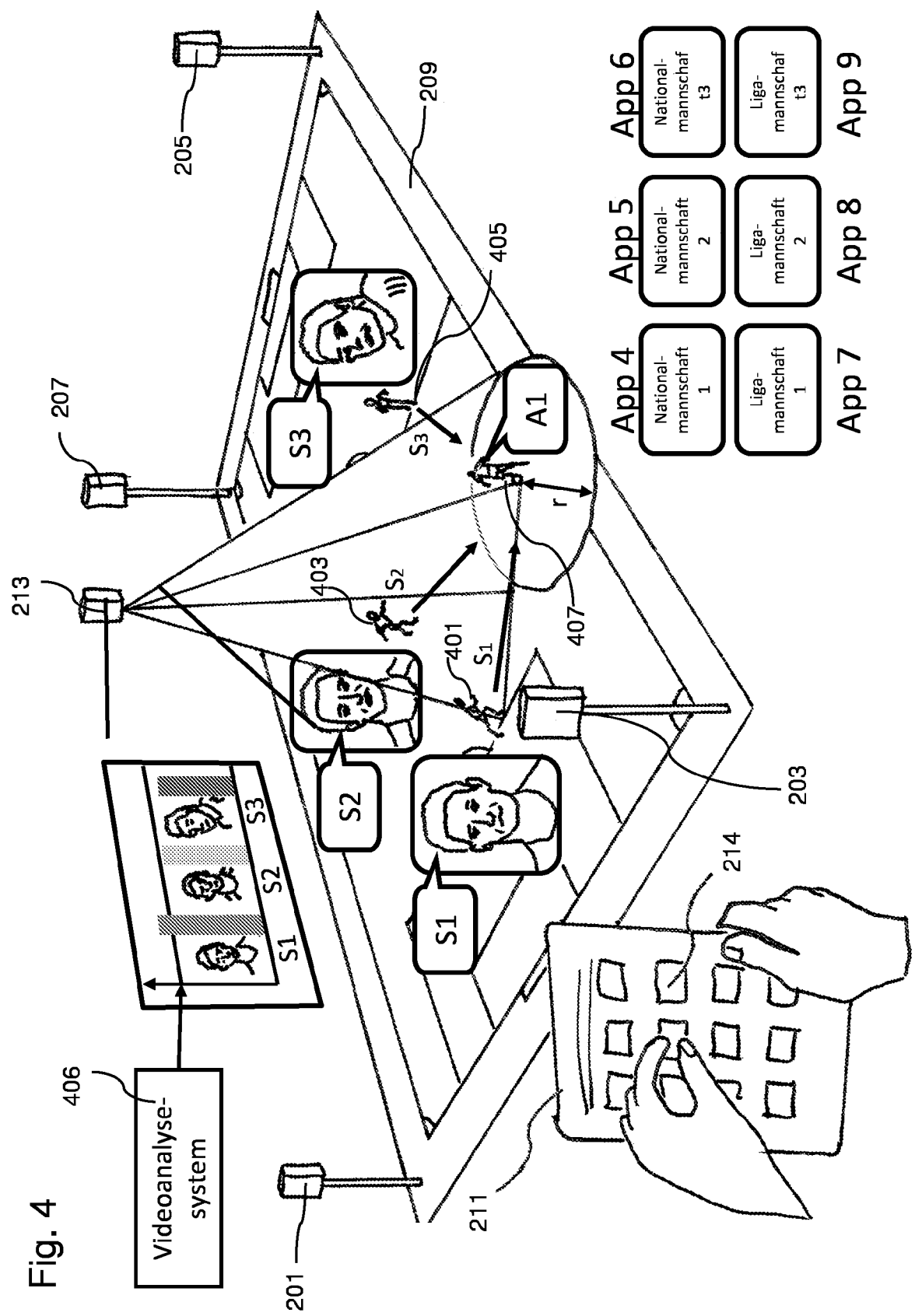
FIG. 4 shows a system for supporting a movement exercise in accordance with a further embodiment.

FIG. 4 shows a system for supporting a movement exercise in accordance with a further embodiment. Players 401 (S1), 403 (S2), 405 (S3) and 407 (A1) situated on the pitch 209 perform training with a ball 409 which, for example, is with player 407, who is an attacker. By way of example, players 401, 403 and 405 can be understood to be objects within the meaning of the present description. By way of example, the indication apparatus 213 can produce signals which transmit a signal containing information relating to his/their intended position to players 401 to 405 or to only one of players 401, 403, 405. The information relating to the intended position can be indicated to the respective player 401, 403, 405 by tactile or acoustic means, or by means of a vibration. To this end, the detection apparatus 213 may have e.g. a vibration module or a loudspeaker, which can be attached to the respective players 401 to 405. The system can furthermore comprise a video analysis system 406.

The exemplary embodiment depicted in FIG. 4 elucidates the group tactic against the ball by means of so-called pressing.

In modern association football, defending already starts deep in the opposition half. By way of example, if an attacker of the opposing team (A1) comes into possession of the ball, the object of the opponents (S1-S3) surrounding him lies in attacking the player A1 as aggressively as possible in order themselves to regain possession of the ball. This is referred to as pressing. The aggression with which a player performs pressing can be measured and assessed by means of the magnitude of the acceleration. If the database now comprises reference values with respect to the acceleration behavior in pressing situations for national and club teams and the world's best association football players, these can be employed for use in real-time feedback training, coaching and learning as intended values. The sequence in a real-time feedback training situation would be as follows in accordance with one embodiment:

1) On a tablet PC, smartphone, PC notebook or any other setting and display unit of the determination apparatus 211, a coach selects the reference values from the database which should be used for comparison in order to arrive at the actual/intended value differences. Apps 4, 5, 6 refer to the standard values of national teams and apps 7, 8, 9 refer to reference values of club teams.
2) By way of example, the coach holds a pushbutton in his hand, with which he can control the time at which pressing should be carried out by the training group. When the coach presses this button, the indication apparatus 213 projects a light cone with radius r around the player with the ball; there likewise is an acoustic signal by means of the PA system and/or mini headphones and/or loudspeaker systems situated on the body. Additionally, depending on setup, there is also tactile feedback by means of a vibration system which can be controlled in terms of frequency and amplitude.
3) If one of the players now approaches the opponent with the ball with acceleration values which deviate too strongly from the reference values, this in turn can be reported back to the player by means of the above-described real-time feedback processes.
4) Once the activity is complete, the indication apparatus 213 can project the intended values, actual values and the intended/actual value difference onto a surface and/or indicate the result on a tablet PC and/or a smartphone or any other control and visualization unit.

Figure 5:
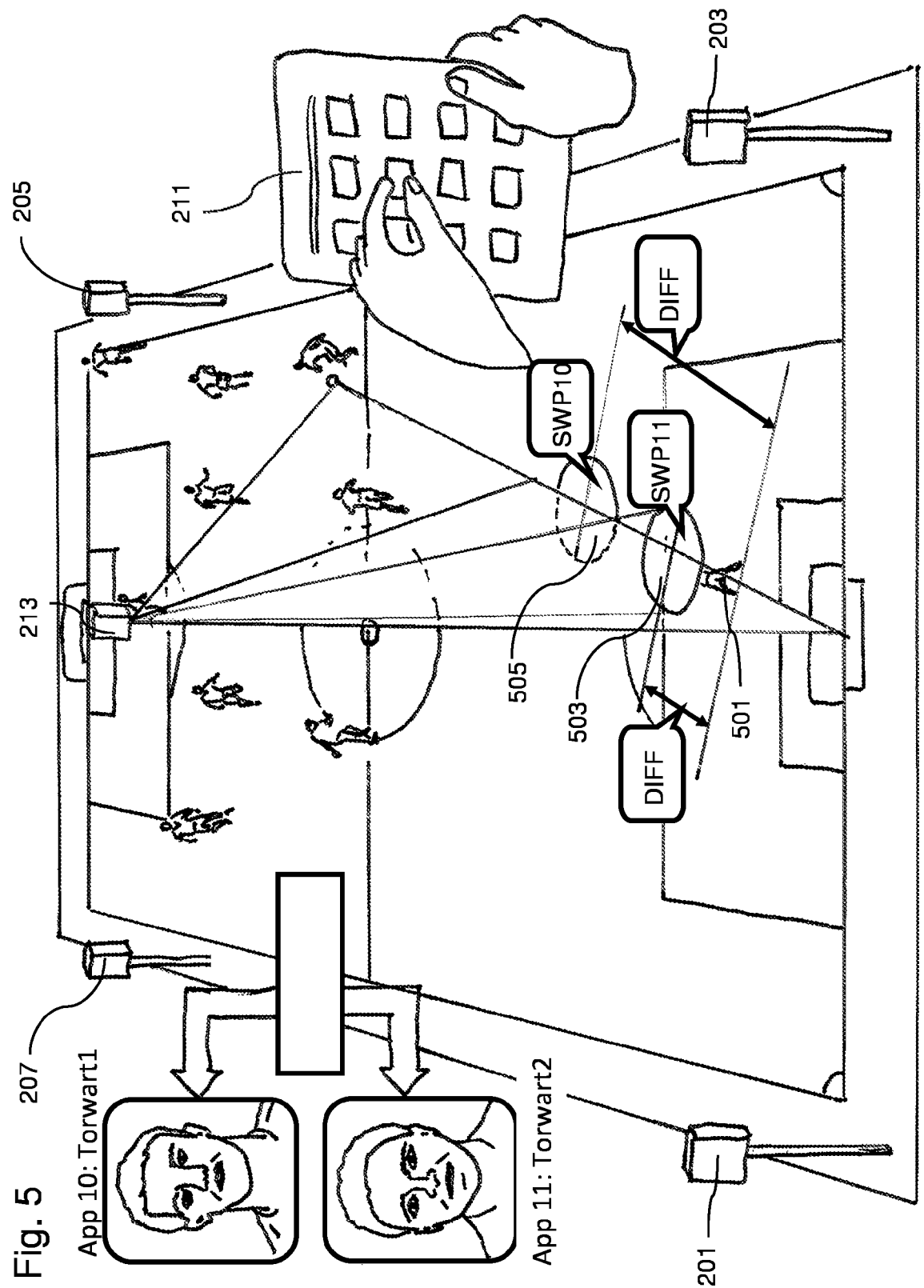
FIG. 5 shows a system for supporting a movement exercise in accordance with a further embodiment.

FIG. 5 shows a system in accordance with a further embodiment, in which e.g. a plurality of items of information relating to intended positions 503, 505 can be indicated to a goalkeeper 501.

In the modern game of association football, the goalkeeper should act as a playing along goalkeeper behind the last line of defense. The basic rule that applies here is that the goalkeeper should move along the imaginary center of the goal-center of the ball connection line. In a real-time feedback training or game scenario, this connection line could now be projected permanently onto the pitch or training area during the training or game by means of the indication apparatus 213. By means of this real-time feedback projection, goalkeepers could learn very quickly to move on the imaginary goal-ball line. In addition to the visual feedback, there could also be acoustic and tactile feedback if the intended/actual value differences exceed certain limit values. The coach, or goalkeeper, for example has the option of deciding with respect to which statistical standard values stored in the database the actual/intended value difference is intended to be calculated. To this end, values which can be obtained in a manner known per se are stored in the database from the analysis of video sequences of the typical behavior of a certain goalkeeper. By way of example, the intended value position of the goalkeeper is determined in such a way that the mean distance between the goalkeeper and the geometric centroid of the team is established by empirical statistical methods, for example from 100 typical video scenes from the past, and stored in the database. This intended value is now put into a mathematical relationship with the centroid of the training or playing team, which is to be detected permanently, and the result is depicted visually in real time during the training or match. This is how the intended value position of the goalkeeper, which can be switched on by the app 10, would be projected dynamically in real time onto the pitch or training field in the form of a circular area (SWP 10). Analogously, the typical behavior of a different goalkeeper could also be depicted on the pitch in real time (SWP 11).

Figure 6:
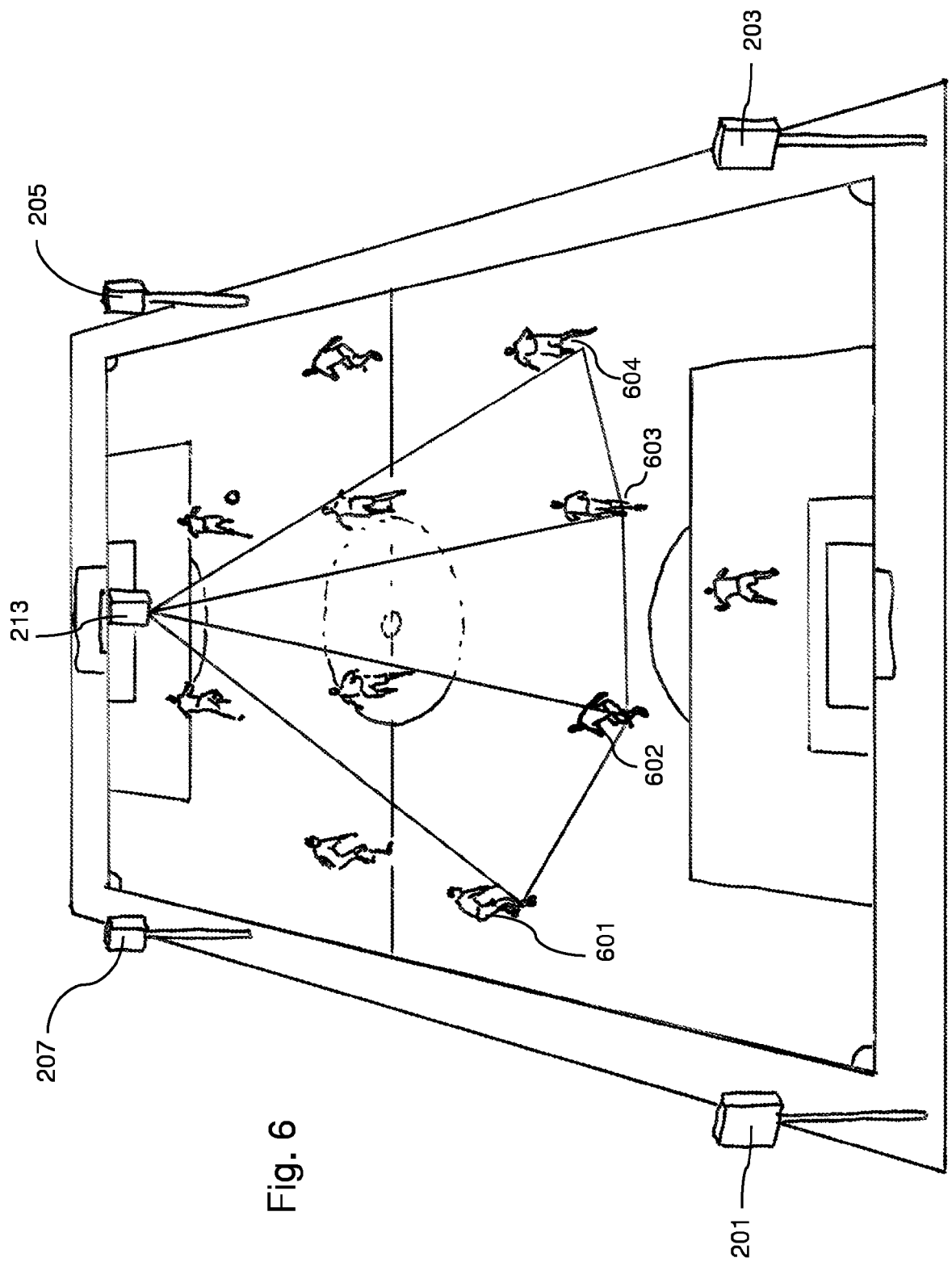
FIG. 6 shows a system for supporting a movement exercise in accordance with a further embodiment.

FIG. 6 shows a system in accordance with a further embodiment, in which players 601-604 are objects within the meaning of the present description. Here, information relating to his/their individual intended position as a function of actual positions of the remaining players is indicated to at least one or more of the players 601. By way of example, in this case, a centroid, for example a geometric centroid, can be determined from the actual positions of the remaining players in order to indicate his individual intended position to the respective player 601.

In accordance with one embodiment, the distance between the players can be monitored in this way. By way of example, the distance between player 601 and player 602 is too large, and so information can be output that this distance is to be reduced such that it corresponds to the intended distance as intended position. By way of example, the intended distance is predefined or emerges from model approaches, which may be deterministic and/or empirical statistical and which keep the intended positions of the players dynamically available in real time.

Figure 7:
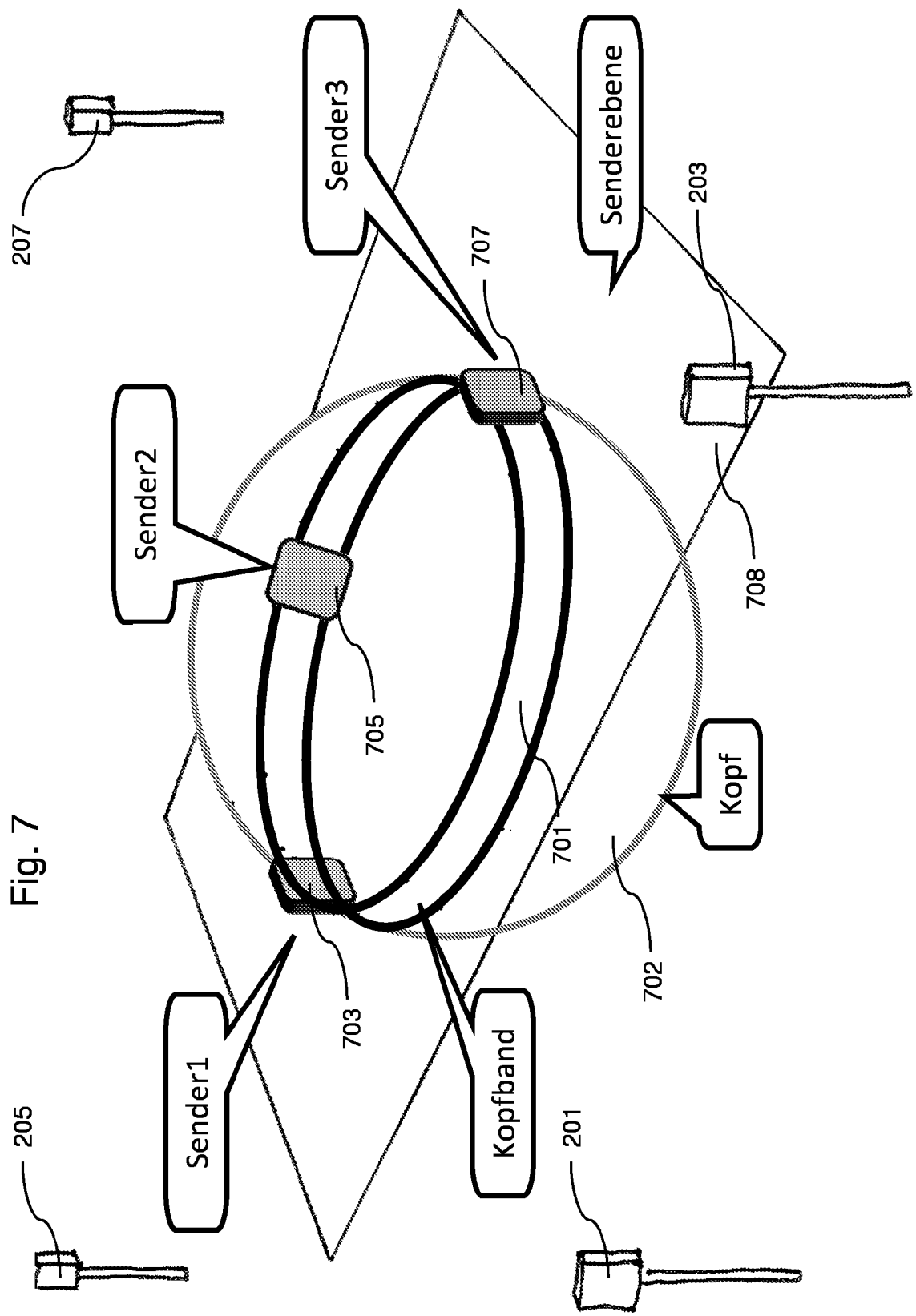
FIG. 7 shows a system for supporting a movement exercise in accordance with a further embodiment.

FIG. 7 shows a system in accordance with one embodiment, in which an indication apparatus 701 is arranged e.g. in a headband which can be arranged on or attached to the head of a player. By way of example, the head of the player can be understood to mean an object within the meaning of the present description. By way of example, the indication apparatus 701 can comprise three transmitters 703, 705, 707, which transmit transmission signals to the detection apparatuses 201, 203, 205 and 207 and which are arranged in a transmitter plane 708. The detection apparatuses 201 to 207 detect the actual position of the head 702, for example a rotational position of the head, on the basis of these signals. A determination apparatus (not depicted in FIG. 7) can produce information relating to an intended position of the head 702 on the basis of the current actual position of the head 702, since the latter, for example, should still be rotated more to the right. By way of example, this can be indicated by means of optical, acoustic or tactile means. In accordance with one of the embodiments, provision can be made for only one, two or three, or more of the detection apparatuses 201 to 207.

Figure 8:
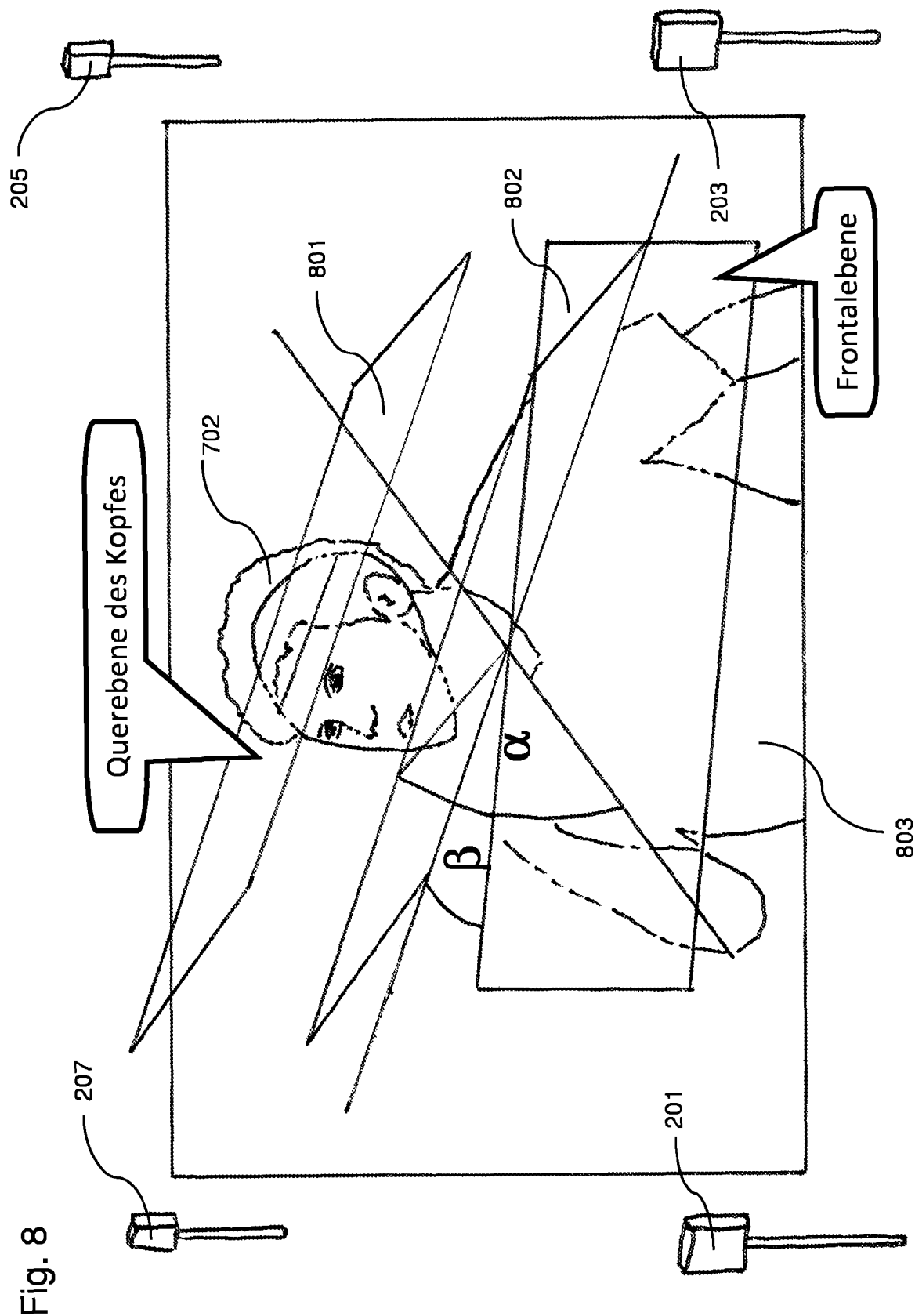
FIG. 8 shows a system for supporting a movement exercise in accordance with a further embodiment.

FIG. 8 elucidates the method of operation of the system, depicted in FIG. 7, with a transversal plane 801 of the head 702, which can correspond to the transmitter plane 801, and also with a frontal plane 802 of the player 803. By way of example, the indication apparatus can indicate a rotation of the head 702 in the transversal plane 801 or a positioning of the head 702 with respect to the frontal plane 802.

In accordance with one embodiment, the position localization system with the detection apparatuses 201, 203, 205, 207, etc. calculates and detects the actual positions of three different instances of positioning of the head of a human in real time. From this, the system calculates the transversal plane of the head. The system likewise detects three different positions of the torso of the human and calculates the frontal torso plane of the human therefrom in real time. From the position of the two planes, the system calculates angles alpha and beta.

Figure 9:
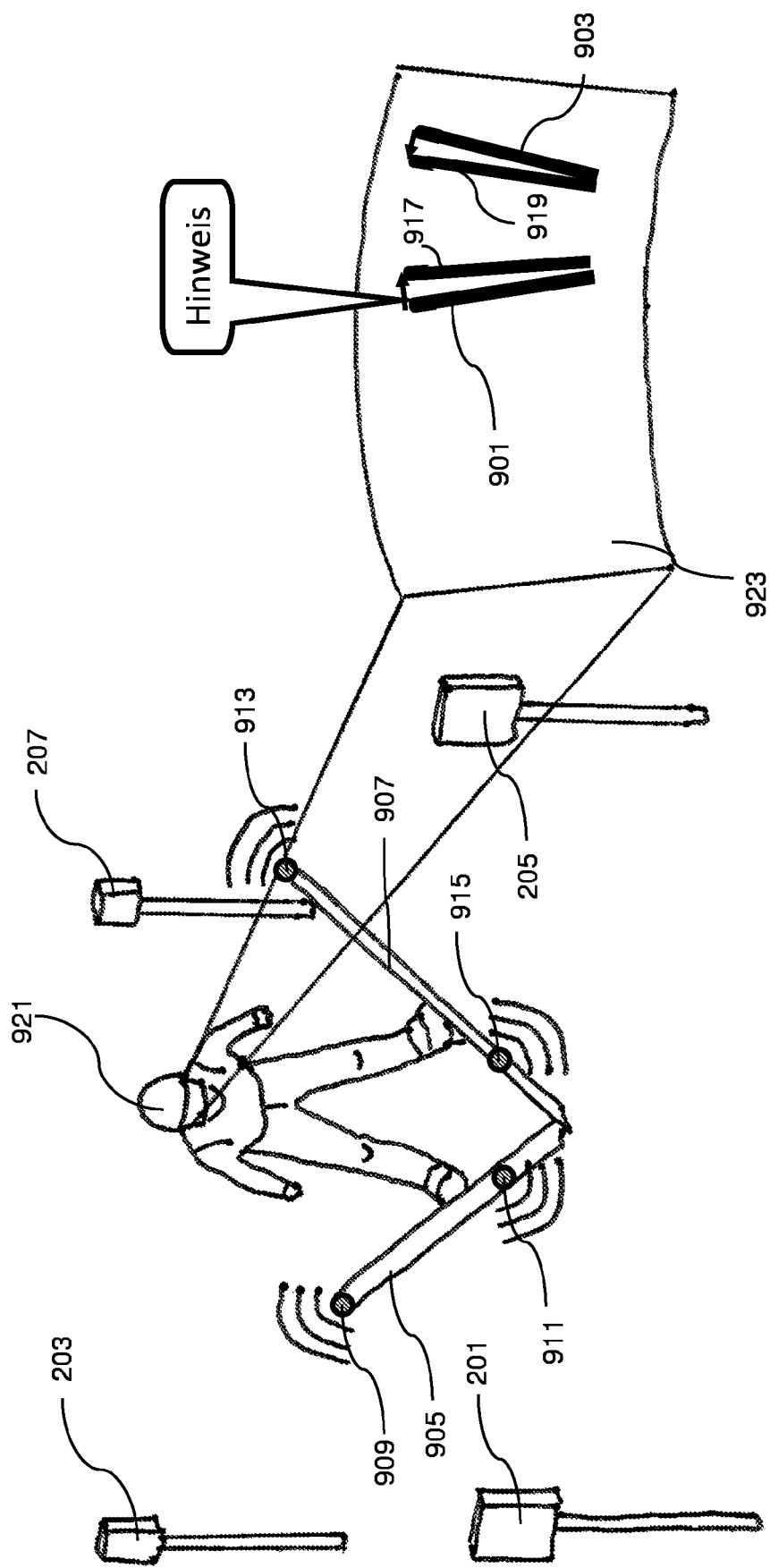
FIG. 9 shows a system for supporting a movement exercise in accordance with a further embodiment.

FIG. 9 shows a system for supporting a movement exercise during ski jumping, in which the actual positions 901, 903 of the skis are detected by means of the detection apparatuses 201, 205, 207 and 209. To this end, each ski 905, 907 can be provided with one or more position sensors 909, 911, 913, 915. By way of example, the position sensors can be arranged in pairs on the skis 905, 907, wherein respectively one of the position sensors 909, 913 is arranged in the front region of the ski, for example on a ski tip, and wherein the other position sensor 911, 915 is respectively arranged e.g. in the heel region of the ski or in the rear region of the ski, preferably at the end of the ski. Intended positions 917, 919 can be calculated on the basis of the actual positions 901, 903 and said intended positions can be projected onto a helmet visor 923 by means of an indication apparatus, which can e.g. be integrated into a helmet 921. Thus, the ski jumper is able to correct the positioning of the skis 905, 907 with respect to one another or with respect to the intended position during the ski jump.

In accordance with one embodiment, the position localization system with the detection apparatuses 201, 203, 205, 207 detects and calculates the positioning of the skis during the ski jump in real time. The machine transmits the actual position in the form of a red line onto a special visor integrated into the jump helmet in real time. At the same time, the system likewise projects the intended position onto the visor. The intended position is that position of the skis in space which would result in the greatest jump distance in accordance with a biomechanical model resulting from permanently detected influencing variables.

Figure 10:
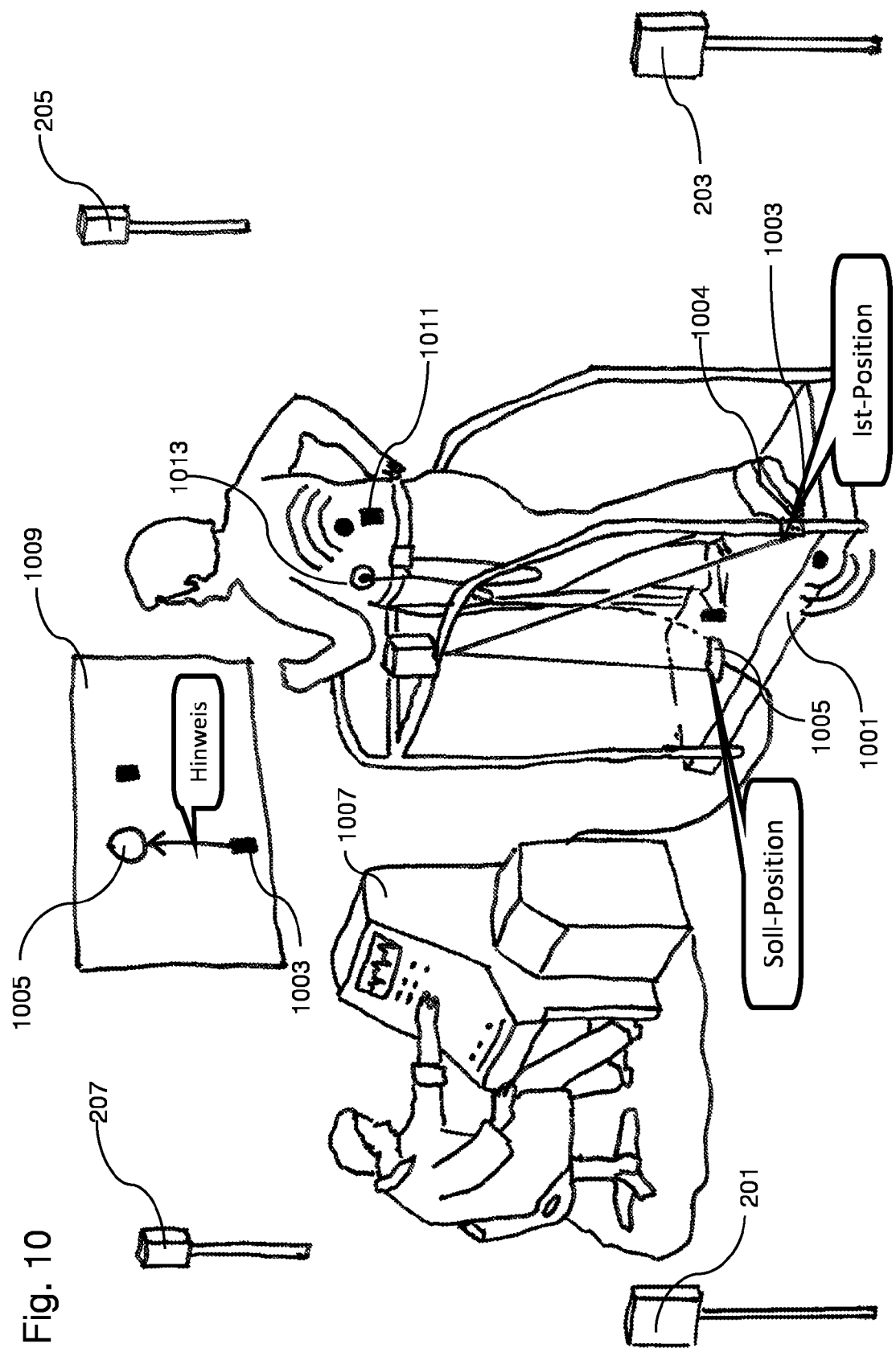
FIG. 10 shows a system for supporting a movement exercise in accordance with a further embodiment.

FIG. 10 shows a system for supporting a movement exercise in the field of rehabilitation, in which e.g. a rehabilitation patient, who is situated on a treadmill 1001, is provided with information relating to an intended position of a foot 1004, which can be understood to be an object, proceeding from an actual position 1003 of the foot. To this end, a determination apparatus, for example housed in a console 1007 of the system, can determine the intended position 1005. An indication apparatus can provide optical information, for example on a display 1009, relating to the intended position 1005 of the foot 1004. Alternatively or additionally, the intended position can also be projected onto the treadmill. In accordance with one embodiment, the information can be indicated in a tactile manner by means of a vibrator 1011, which, for example, can be attached to the body of the rehabilitation patient. By way of example, this renders it possible to produce a vibration signal as information relating to the intended position, the vibration frequency of which vibration signal for example depending on a difference between the actual position 1003 and the intended position 1005.

The rehabilitation patient can be efficiently supported in his movement exercise in this manner. Moreover, a body parameter sensor 1013 can be provided to the patient, said sensor detecting body parameters, such as e.g. heart rate or pulse frequency, and transferring these to the system console 1007. The determination apparatus can determine the intended position 1005 as a function of at least one body parameter. This allows the determination of the intended position 1005 to be adapted to the physical conditions of the rehabilitation patient.

In accordance with one embodiment, the position localization system with the detection apparatuses 201, 203, 205, 207 calculates and detects the positioning of the feet of a patient with a movement disorder, for example a state after apoplexy, in real time during walking. The machine sends the actual position of the tips of the foot in the form of red points to the floor of the treadmill in real time and, virtually, to a monitor which is situated in front of the patient, level with the eyes. At the same time, the system likewise projects the intended position of the tips of the foot in the form of a green point onto the treadmill and the monitor. The intended position is that position according to a biomechanical model which the patient can reach without maximum effort due to the calculation with permanently detected influencing variables.

Figure 11:
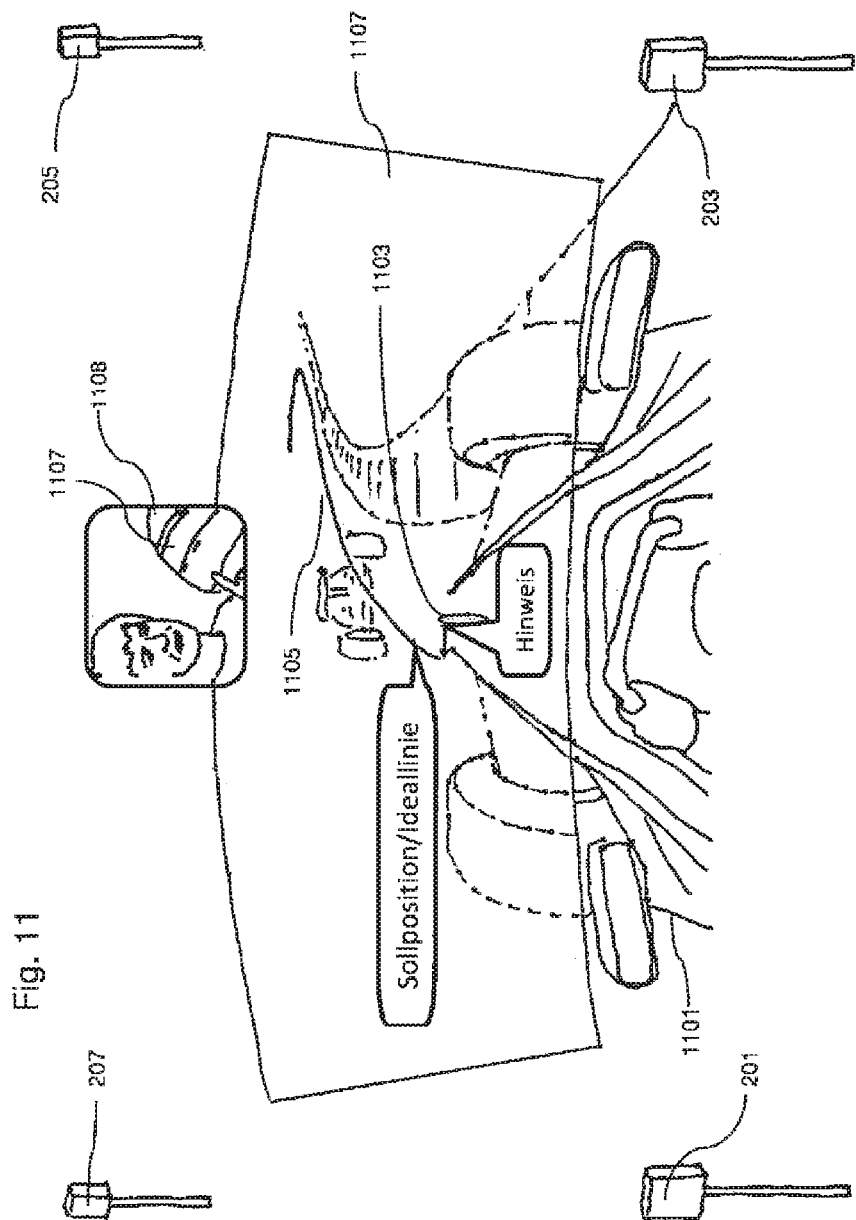
FIG. 11 shows a system for supporting a movement exercise in accordance with a further embodiment.

FIG. 11 shows a system in accordance with one embodiment with a vehicle 1101, for example a racing vehicle, as object. By way of example, the vehicle 1101 can comprise a position transmitter, the transmission signals of which are received by detection apparatuses 201 to 207. A determination apparatus, not depicted in FIG. 11, can establish the current actual position 1103 of the vehicle 1001 on this basis in a manner known per se. By way of example, an indication apparatus can comprise a projector which projects information relating to the determined intended position 1105, for example in the form of an ideal driving line, onto a visor 1107 of the driver's helmet 1108. However, the projection can also be cast onto a windscreen of the vehicle.

In accordance with one embodiment, the position localization system calculates and detects the actual position of a race car during a race by means of the detection apparatuses 201, 203, 205, 207 in real time. The machine transmits the intended position of the car in real time to a special visor in a virtual manner, which visor is integrated into the helmet of the pilot. By way of example, the intended position is that location on the ideal line which would have to be assumed by the vehicle at the time of detecting the actual position in order to realize the fastest lap time.

Figure 12:
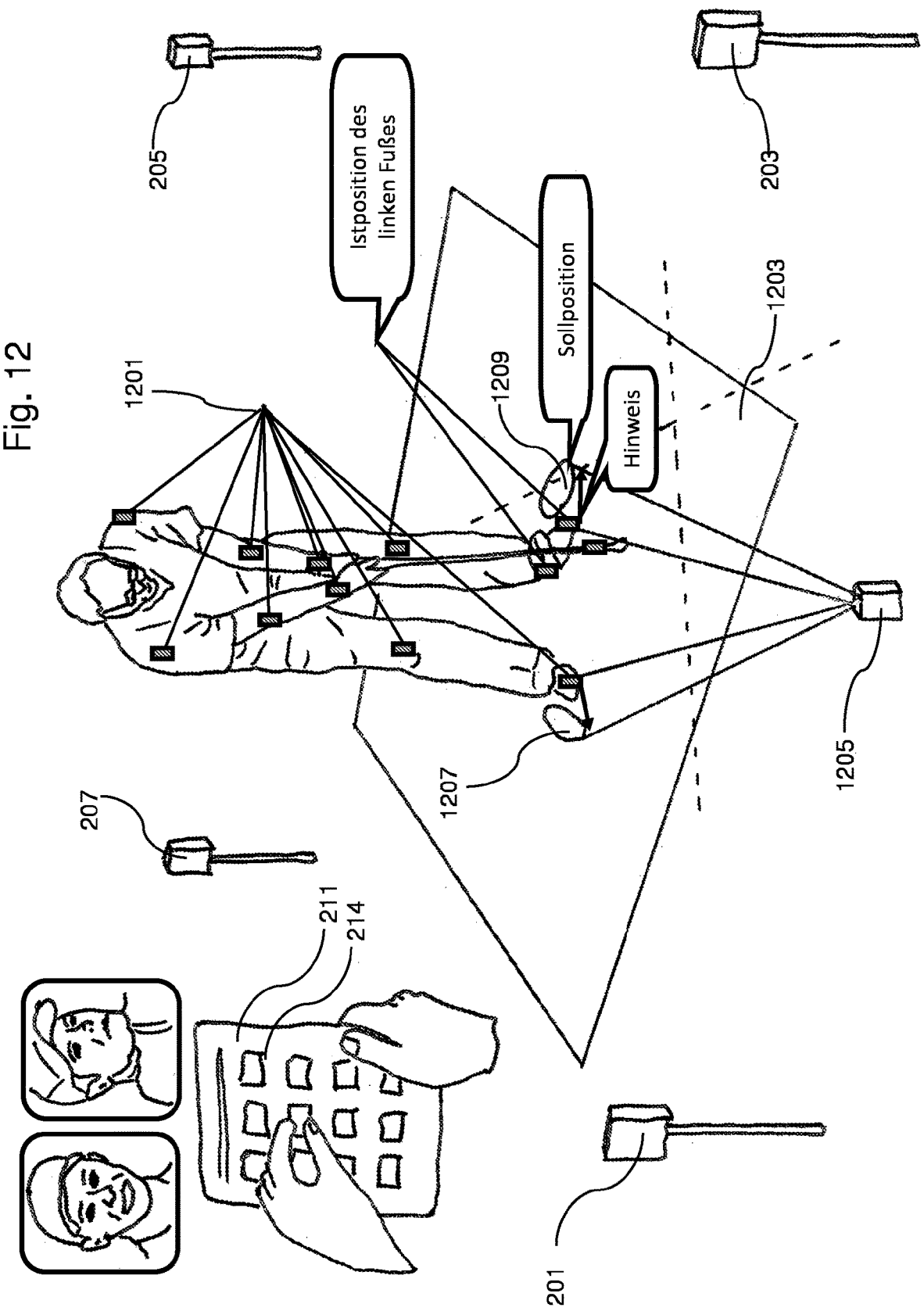
FIG. 12 shows a system for supporting a movement exercise in accordance with a further embodiment.

FIG. 12 shows a system for supporting a movement exercise in accordance with an embodiment which is directed to golf. To this end, the determination apparatus comprises a plurality of transmitters 1201, which are arranged on different body parts of a golfer, for example on knees, wrists, elbows or upper arms. On the basis of the transmission signals from the position sensors 201, the detection apparatuses 201 to 207 can determine the positioning of the individual body elements, such as the feet, as actual positions. By way of example, the player is situated in a game region 1203, which can be embodied e.g. as a standing plate. By way of example, an indication apparatus 1205 can project intended positions 1207, 1209 of the individual feet of the players onto the standing plate 1203 from above or from below. In accordance with one embodiment, the indication apparatus 1205 can excite luminous elements, such as e.g. light-emitting diodes, which are housed in the standing plate 1203 for indicating the intended positions 1207, 1209.

In accordance with one embodiment, the position localization system with the detection apparatuses 201, 203, 205, 207 calculates and detects the actual positions of different points of the golfer in real time. This also includes the actual position of the feet, which emerges from the connection line between center of the heel and second ray of the toes. The machine indicates the intended position of the feet in real time in the form of a projection onto the standing plate 1203, which may be a transparent (force measuring) plate. The intended position is defined by biomechanical rules in a model combined with statistical characteristics of the world's best golfers. The golfer determines the model according to which the real-time feedback reports the feedback of the intended/actual value difference to the athletes.

Figure 13:
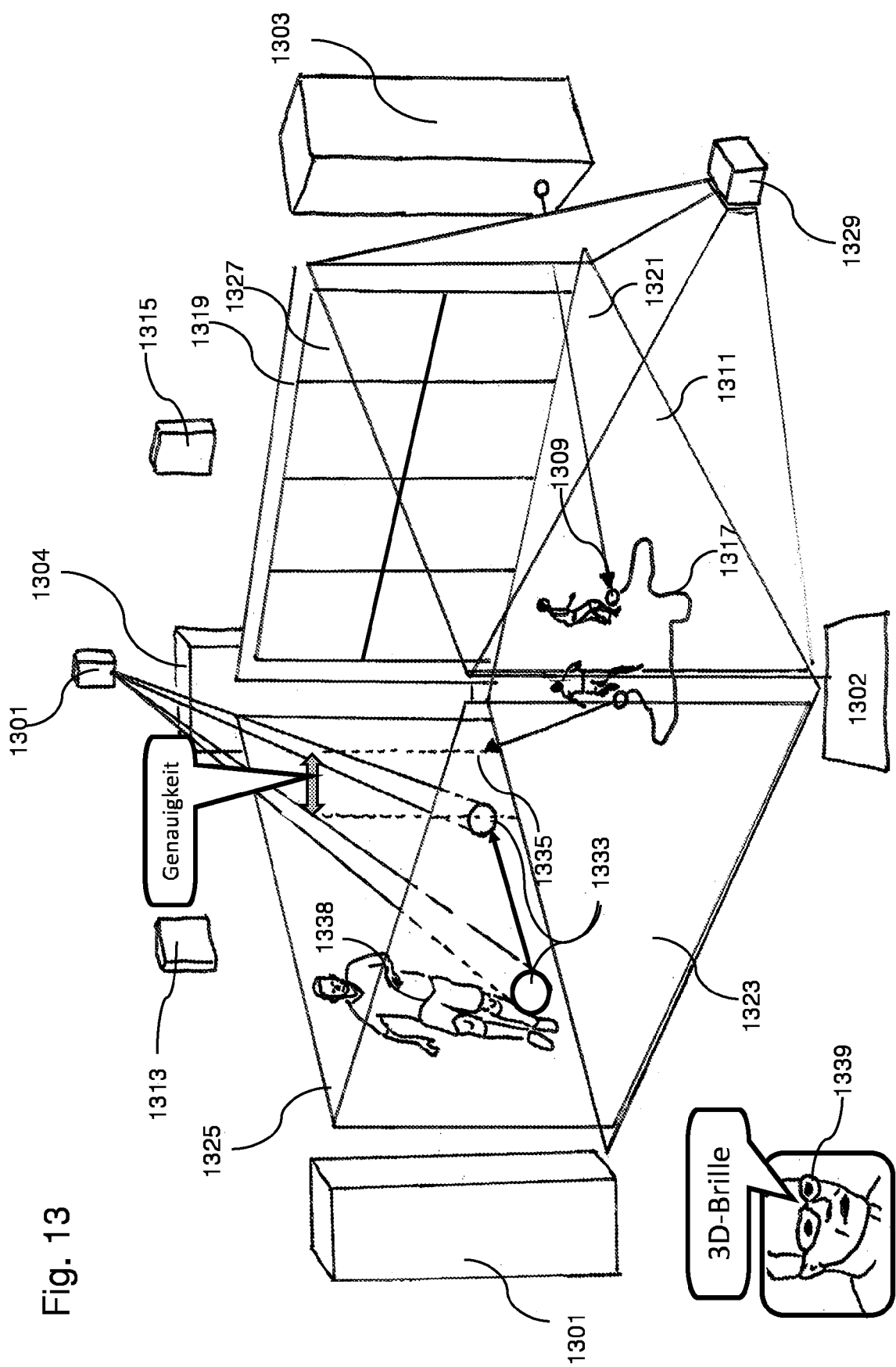
FIG. 13 shows a system for supporting a movement exercise in accordance with a further embodiment.

FIG. 13 shows a system in accordance with one embodiment, in which a movement exercise with a ball, for example with a football, is supported.

The system comprises at least one indication apparatus 1301 and one or more ball providers 1301, 1302, 1303 and 1304, which are respectively embodied to provide a ball 1309 to the pitch 1311. The system comprises at least one determination apparatus 1313, 1315 which is embodied to detect a position of the ball 1309 as actual position of the ball. To this end, the ball 1309 can be embodied to emit a transmission signal which can be received and evaluated in a manner known per se by at least one determination apparatus 1313, 1315 for determining the position. In particular, the at least one determination apparatus 1313, 1315 can be embodied to detect a plurality of positions of the ball 1309, which are depicted in an exemplary manner in FIG. 13 by the trajectory 1317. In this manner, at least one determination apparatus 1313, 1315 can detect a retention time of the ball 1309 at the player who receives the ball 1309 and passes it on. By way of example, the retention time can be detected on the basis of braking, i.e. a negative acceleration, of the ball 1309 at the time when the player receives the ball and a positive acceleration at the time when the player passes the ball on.

The system furthermore comprises at least one ball capturing unit 1319, 1321, 1323, 1325, which is e.g. embodied as a sensor wall which delimits the pitch 1311 at least in part. The sensor walls 1319, 1321, 1323 and 1325 for example comprise sensor areas 1327 which can be equipped with pressure sensors. By way of example, to this end, an indication apparatus 1329 can select an area 1327 in order to indicate an intended position of the ball 1309. By way of example, this can be brought about by illuminating the respective area 1327. This can indicate to the player where he should shoot the ball 1309.

In accordance with an additional or alternative embodiment, the indication apparatus 1301 is provided, which is embodied to project an intended position 1333 of the ball onto one of the sensor walls 1325 in a static or dynamic manner. By way of example, as depicted in FIG. 13, the intended position can be changeable, which is depicted by the arrow. After the ball was passed, the sensor wall 1325 can detect an impact location 1335, for example by pressure, from which deviation 1337 between the intended position and the detected position can be determined. In the case of a localization of the ball and a spatial geometry known to the computer, it is also possible to establish the impact location 1335 without a pressure sensor system. In this case, it is possible to dispense with the pressure sensor system in the sensor wall.

In accordance with one embodiment, the indication apparatus 1329 can project a player figure 1338 onto the sensor wall 1325 in order to simulate a teammate. This simulation can be three-dimensional, for the purposes of which the player can be equipped with e.g. three-dimensional spectacles 1339, e.g. 3D glasses.

An advantage of the concept described herein consists of the fact that not only can it be transferred to a plurality of ballgames but it also can be used in other sports (climbing) or in fields away from sports, in which motor learning is important or motor learning plays a role. Furthermore, the same system can e.g. be broken down to smaller spatial arrangements and such systems can be used for constructing new instruments for fairground entertainers at fairs. The system can likewise be used in theme parks for building new attractions. Moreover, the system can be used for the rehabilitation of stroke patients or other people who have to relearn movements because the permanent real-time feedback greatly shortens learn times compared to trial and error learning by trial and error. Since this technology allows performance profiles of professional footballers/other athletes to be created in respect of the technical/tactical ability and skill level, it is to be expected that professional clubs will comprehensively diagnose their players in the machine prior to buying or selling. Due to horrendous sums for sales, correspondingly high amounts are to be expected for diagnostic service offering within the illustrated meaning.

In accordance with one embodiment, provision is made for a real-time localization system of one or more active or passive markers, which can be fastened to one or more positions of one or more subjects and/or one or more objects. By way of example, the real-time localization system comprises at least one indication apparatus. The real-time localization system can be an infrared cinematographic system, which operates with passive retroreflective markers; however, it can also be a video-based tracking system or a radio-based localization system which operates using active transmitters and corresponding receiver technology. However, it can also be any other active or passive localization system.

Furthermore, provision can be made for a real-time biosignal recording and transmission system for synchronized derivation and transmission of physiological signals, e.g. heart rate, heart rate variability, body temperature, respiratory frequency, skin resistance, electrolyte composition, with the aforementioned localization data. Moreover, it is also possible to consider technical data such as air pressure and/or rotation and/or acceleration.

Furthermore, it is possible to provide a database system, which can be filled with external and/or internal data. This database is permanently extended, either with external data or internal data. By way of example, external data are data from matches or training units or other events or incidents, which were recorded and analyzed by video or by a different data acquisition technique. The database also records values from other sources. By way of example, performance-diagnostic variables from laboratory or the so-called "Feldstufentest" endurance test or else anthropometric data from measurements with a body scanner, etc. However, the database is also permanently and systematically extended by data which emerge from the inherent recordings (actual values). These data are referred to as internal sources.

Furthermore, provision can be made for a rule system which is continuously extended by the implementation of expert knowledge. Sports scientists, sports medicine specialists, engineers, association football coaches, etc. can be experts.

Furthermore, provision can be made for a setup module which is controlled by a PC or Tablet PC or smartphone or another control instrument. This setup module determines which internal and external sources are used for the intended/actual value comparison for a training, match or observation unit. Likewise, the module is used to set the specification for a real-time feedback system.

The setup module, the rule system and the database system can be implemented in the determination apparatus.

Furthermore, provision can be made for a real-time feedback system, which comprises the indication apparatus and which transmits intended values and/or actual values and/or intended/actual value differences to the subject or the subjects in real time in the form of optical/visual and/or acoustic and/or tactile signals. Visual signals can be the following: a laser projection system or another optical projection system or a screen or another optical/visual display method, an acoustic system, comprising a mini headphone or a PA system or a loudspeaker system situated on the body, or at least one vibration instrument, which can be carried on the body at defined positions.

From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The invention claimed is:

1. A system for supporting a movement exercise with an object, in real time, comprising:
   a position localization system comprising:
      a detection apparatus for detecting an actual position of the object, wherein the detection apparatus is embodied to determine a plurality of further actual positions of a plurality of further objects, wherein the detection apparatus comprises a receiver, wherein the object and each further object comprises a respective transmitter, wherein the actual position and the further actual positions are represented by respective digital position data, wherein the plurality of further objects is formed by a plurality of players;
      a determination apparatus for determining an intended position of the object, wherein the intended position is represented by digital position data, wherein the determination apparatus is embodied to determine a centroid of the further actual positions, wherein the determination apparatus is embodied to determine the intended position based upon a rule and as a function of the actual position of the object and the centroid; and
      an indication apparatus for indicating information relating to the intended position if the actual position differs from the intended position, wherein the indication apparatus is embodied to indicate the information relating to the intended position on an electronic display, wherein the indicated apparatus is embodied to actuate the display of a mobile device for indicating the information relating to the intended position.

2. The system of claim 1, wherein the object is embodied to emit a position signal, and wherein the detection apparatus is embodied to receive the position signal and determine the actual position of the object based upon the received position signal.

3. The system of claim 1, wherein the detection apparatus is embodied to receive a reflection signal, reflected at the object and determine the actual position of the object based upon the reflected reflection signal.

4. The system of claim 3, wherein the detection apparatus is embodied to emit a transmission signal in order to produce the reflection signal.

5. The system of claim 1, wherein the determination apparatus is embodied to determine a predetermined position of the object as the intended position.

6. The system of claim 1, wherein the object is a ball and wherein the determination apparatus is embodied to determine a sensor area of a sensor wall as the intended position.

7. The system of claim 6, wherein the determination apparatus is embodied to determine at least one of (i) the intended position as a function of the actual position of the object and a geometric characteristic of an area within which the object can be moved, and (ii) the intended position as a function of the actual position of the object in relation to a geometric characteristic of a pitch.

8. The system of claim 1, wherein the determination apparatus is embodied to determine the intended position as a sequence of successive auxiliary positions.

9. The system of claim 1, wherein the detection apparatus is embodied to determine a further actual position of a further object and wherein the determination apparatus is embodied to determine the intended position of the object as a function of the further actual position.

10. The system of claim 9, wherein the determination apparatus is embodied to determine the intended position based upon a predetermined rule which links the intended position to an actual position.

11. The system of claim 9, wherein the object is a set of skis.

12. The system of claim 1, wherein the determination apparatus is embodied to determine the intended position as a function of the geometric centroid based upon a predetermined rule which links intended positions to geometric centroids.

13. The system of claim 1, wherein the indication apparatus is embodied to indicate the intended position itself as at least one of (i) information relating to the intended position, (ii) information relating to the positioning of the intended position with respect to positioning of the object and (iii) as information relating to a difference between the actual position and the intended position.

14. The system of claim 1, wherein the indication apparatus is embodied to indicate the information relating to the intended position by at least one of acoustic, optical, acousto-optical, tactile, vibration, and pressure.

15. The system of claim 1, wherein the object is at least one of a match ball and a puck, the indication apparatus comprises a sensor wall for detecting an object impinging on the sensor wall and wherein the indication apparatus is embodied to indicate an area of the sensor wall as information relating to the intended position by at least one of a visual accentuation, a luminous, illuminated area, and acoustic accentuation.

16. The system of claim 1, wherein the indication apparatus comprises at least one of a visor and a projection apparatus, and wherein the indication apparatus is embodied to indicate the information relating to the intended position on at least one of the visor and projection onto a projection area by the projection apparatus.

17. The system of claim 16, wherein the visor is a visor of a skiing helmet and wherein the indication apparatus is embodied to indicate the information relating to the intended position with respect to at least one of the actual position and at least one of the skis in respect of the other ski on the visor.

18. The system of claim 16, wherein the object is at least one of a vehicle and a motor vehicle, and wherein the indication apparatus is embodied to indicate the information relating to the intended position as at least one of an ideal vehicle line on a visor of a helmet and as projection on a windscreen.

19. The system of claim 1, wherein the object is at least one foot of a user and the indication apparatus is embodied to indicate the information relating to the intended position of at least one of the feet onto an area of ground, on which the user can be positioned.

20. The system of claim 1, wherein the indication apparatus is embodied to project the information relating to the intended position onto a pitch by a light.

21. The system of claim 1, wherein the determination apparatus is embodied to determine the intended position as a function of a body parameter.

22. The system as of claim 1, wherein the indication apparatus is embodied to indicate the information relating to the intended position as a function of a body parameter.

23. The system of claim 1, wherein the object is a piece of playing equipment.

24. The system of claim 1, wherein the object is a user.

25. The system of claim 1, wherein the object is the head of a user, wherein the detection apparatus is embodied to detect a plurality of position signals indicating a head position, wherein the determination apparatus is embodied to determine a transversal plane of the head as the actual position of the head and wherein the indication apparatus is embodied to indicate information relating to the intended position situated in the transversal plane by at least one of acoustic, optical, and tactile means.

26. The system of claim 25, wherein the determination apparatus comprises a plurality of position sensors arranged on the head of a user, for determining the position and outputting position signals, and a plurality of luminous elements for indicating the information relating to a rotational direction of the head in the transversal plane.

27. The system of claim 1, wherein the determination apparatus comprises at least one position determination apparatus for detecting the actual position.

28. The system of claim 1 further comprises an object provider for providing the object.

29. The system of claim 1 comprises a plurality of detection apparatuses for detecting the actual position.

30. A method for supporting a movement exercise with an object in real time using a positioning localization system, comprising a detection apparatus comprising:

detecting an actual position of the object, wherein the detecting step includes determining a plurality of further actual positions of a plurality of further objects, wherein the detection apparatus comprises a receiver, wherein the object and each further object comprises a respective transmitter, wherein the actual position and the further actual positions are represented by respective digital position data, wherein the plurality of further objects is formed by a plurality of players;

determining an intended position of the object, wherein the intended position is represented by digital position data, wherein the step of determining the intended position of the object includes determining a centroid of the further actual positions, and wherein the step of determining the intended position of the object is based upon a rule and as a function of the actual position of the object and the plurality of the centroid; and indicating information relating to the intended position if the actual position differs from the intended position, wherein the step of indicating information is embodied to indicate the information relating to the intended position on an electronic display, wherein the step of indicating information is embodied to actuate the display of a mobile device for indicating the information relating to the intended position.

* * * * *